United States Patent [19]

Prinz et al.

[11] Patent Number: 5,158,878
[45] Date of Patent: Oct. 27, 1992

[54] TYPE II RESTRICTION ENDONUCLEASE SWAI

[75] Inventors: Barbara Prinz, Friedrichshafen; Max Lechner; Bruno Frey, both of Penzberg; Michael Jarsch, Bad Heilbrunn, all of Fed. Rep. of Germany

[73] Assignee: Boehringer Mannheim GmbH, Mannheim, Fed. Rep. of Germany

[21] Appl. No.: 695,936

[22] Filed: May 6, 1991

[30] Foreign Application Priority Data

May 7, 1990 [DE] Fed. Rep. of Germany ....... 4014524

[51] Int. Cl.⁵ .................. C12P 19/34; C12N 9/22
[52] U.S. Cl. ........................ 435/91; 435/199; 435/882
[58] Field of Search .................. 435/199, 91

[56] References Cited

FOREIGN PATENT DOCUMENTS

3823451  1/1990  Fed. Rep. of Germany .

OTHER PUBLICATIONS

Kessler C. et al. (1990) Gene 92, 1, 41, 232.
Cremer, J. et al. (1990) Chem. Abstrs. 112:234001j.

*Primary Examiner*—Charles L. Patterson, Jr.
*Attorney, Agent, or Firm*—Felfe & Lynch

[57] ABSTRACT

The novel type II restriction endonuclease SwaI has the following recognition sequence:

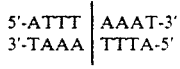

5'-ATTT | AAAT-3'
3'-TAAA | TTTA-5' and preferably cleaves at the cleavage site indicated by the line. It is preferably obtainable from microorganisms of the genus Staphylococcus.

10 Claims, No Drawings

TYPE II RESTRICTION ENDONUCLEASE SWAI

FIELD OF THE INVENTION

The invention concerns the new type II restriction endonuclease SwaI, a process for its isolation and its use.

BACKGROUND AND PRIOR ART

Type II restriction endonucleases are endodeoxyribonucleases which are able to recognize and cleave particular DNA sequences. In this process one phosphodiester bridge in each polynucleotide strand of the target sequence is hydrolyzed. Type II restriction endonucleases are thus of value for the analysis of DNA molecules. Although type II restriction endonucleases are known which are specific for numerous DNA sequences, there is still a need for further type II restriction endonucleases which are specific for DNA sequences that up to now have not been recognized by any of the known restriction endonucleases. The object of the present invention is therefore to provide a new restriction endonuclease which is able to specifically recognize and cleave a sequence which has previously not been recognized by any such enzyme.

SUMMARY OF THE INVENTION

This object is achieved according to the present invention by a type II restriction endonuclease having the recognition sequence

```
5'-ATTT  AAAT-3'
3'-TAAA  TTTA-5'
``` and the cleavage site indicated by the line.

DETAILED DESCRIPTION OF PREFERRED EMBODIMENTS

The new restriction endonuclease according to the present invention, which is denoted SwaI hereafter, has a temperature optimum at 25° C. The enzyme has good activity between pH 7.0 and pH 8.0 in 50 mmol/l Tris/HCl buffer with 1.0 mmol/l DTE (dithioerythritol), 10 mmol/l MgCl and 100 mmol/l NaCl. The pH optimum is at pH 7.5.

The recognition sequence can be confirmed by the complete digestion of the DNA's of the viruses SV40 and adeno 2, of the phages lambda, T7 and phiX174 and of the phage derivative M13mp7 as well as of the plasmids pBR322 and pBR328. These DNA molecules are treated with SwaI.

Table 1 shows a comparison of the cleavage specificity observed experimentally with a cleavage site specificity determined by a computer for an enzyme which recognizes the following sequence:

5'-ATTTAAAT-3'

TABLE 1

| DNA | Number of cleavage sites determined experimentally | Number of cleavage sites determined by computer analysis | Fragment lengths determined experimentally (base pairs) | Fragment lengths determined by computer analysis (base pairs) | Cleavage positions determined by computer analysis (at base pairs) |
|---|---|---|---|---|---|
| SV40 | 1 | 1 | 5250 | 5243 | 1797 |
| M13mp7 | 1 | 1 | 7200 | 7229 | 6761 |
| PhiX174 | 0 | 0 | 0 | 0 | 0 |
| PBR322 | 0 | 0 | 0 | 0 | 0 |
| pBR328 | 0 | 0 | 0 | 0 | 0 |
| Lambda | 0 | 0 | 0 | 0 | 0 |
| T7 | 1 | 1 | 34000 6000 | 33966 5970 | 5970 |
| Ad2 | 1 | 1 | 28900 7000 | 28904 7033 | 28904 |

The cleavage position within the recognition sequence of the enzyme can be determined on an M13 derivative having this recognition sequence at a distance of ca. 30-200 bases from the binding site of the universal sequencing primer (Messing, J. et al., (1981) Nucl. Acids Res. 9, 309-321). At first sequence reactions according to the dideoxy chain-termination method (Sanger, F. et al., (1977) Proc. Natl. Acad. Sci. U.S.A. 74, 560-564, Messing, J. et al., (1981) Nucl. Acids Res. 9, 309-321) are carried out on the single-stranded DNA of the M13 derivative with the universal sequencing primer.

Parallel to this, the sequencing primer is radioactively labelled at the 5' end with T4-polynucleotide kinase and [$\delta$-$^{32}$P]ATP. After hybridization of this 5' end-labelled sequencing primer to the single-stranded M13 DNA, a partially double-stranded DNA is prepared in a filling in reaction with DNA-polymerase I, (Klenow enzyme) and a deoxynucleotide triphosphate mixture of dATP, dCTP, dGTP and dTTP. This DNA, whose newly synthesized strand is radioactively labelled at the 5' end, is cleaved with the restriction endonuclease SwaI. Half of the cleavage preparation is additionally treated with T4-DNA polymerase in the presence of a mixture of all four deoxynucleotide triphosphates in order to obtain blunt DNA ends.

The analysis of the reaction products is carried out by electrophoresis on sequencing gels (8 mol/l urea, 5% polyacrylamide) and subsequent autoradiography. The results are interpreted according to Brown, N. L. and Smith, M. (Methods in Enzymology 65 (1980) 391-401). The position of the cleavage site is determined by a comparison of the distances of migration of the radioactively-labelled fragments with the sequencing ladder. The samples which were additionally treated with T4 DNA polymerase show a migration of the bands which is identical compared to the sample which was only cleaved with SwaI. This therefore shows that SwaI produces a blunt DNA end.

The cleavage of SwaI has therefore the following specificity within the recognition sequence:

The number of cleavage sites determined experimentally is identical to the number of cleavage sites for the sequence

obtained by computer analysis with the different DNA's (Table I). In addition these data were also compared with the tables in Gene 10 (1980) 357-370.

SwaI is preferably isolated by culturing microorganisms of the genus *Staphylococcus*, preferably of the species *Staphylococcus warneri* and isolating the enzyme from the cells. *Staphylococcus warneri* DSM 5872 is particularly preferred.

The microorganism *Staphylococcus warneri* is deposited at the German Collection for Microorganisms (DSM), Mascheroder Weg 16, 3300 Braunschweig, BRD and has the deposit number DSM 5872.

The usual biochemical methods of purification can be used for the isolation in which the presence of the enzyme in the respective fractions obtained can be easily tested on the basis of the cleavage of its recognition sequence. Adeno 2 DNA is for example suitable as the substrate. The DNA fragments obtained are separated electrophoretically in agarose gels in buffer systems usually used for the fragment separation in the presence of ethidium bromide.

The microorganisms used for the isolation of the enzyme grow aerobically in Brain Heart Infusion Medium from the Difco Company.

The optimal conditions for growth are at a temperature of 37° C., and at a pH between 6.5 and 7.5. The doubling time is about 3 hours.

The enzyme is isolated and purified by the usual chemical and mechanical methods such as by high pressure dispersion, ultrasound or enzymatic lysis. In a preferred embodiment of the process according to the present invention the cells are lysed by means of a French press. The further purification of the supernatant is preferably carried out by means of affinity chromatography and ion-exchange chromatography. Heparin-Sepharose CL-6B (Pharmacia) is for example suitable as the material for the affinity chromatography. Cellulose phosphate (Whatman) is for example suitable as the cation exchanger.

The product available under the name DEAE fast-flow (Pharmacia) is suitable as the anion-exchanger. Other chromatographic materials which are known to the expert are also suitable.

The following Examples elucidate the invention further.

EXAMPLE 1

Staphylococcus warneri DSM 5872 is cultured at 37° C. for 12-15 hours and is harvested at the end of the logarithmic phase. Brain Heart Medium (Difco) is used as the culture medium.

The cell paste (30 g wet weight) is resuspended in 2.4 volumes buffer A (40 mmol/l Tris-HCl, pH 8.0, 0.1 mmol/l EDTA, 7 mmol/l 2-mercaptoethanol), which contains protease inhibitors. Subsequently the cells are lysed by passing them twice through a French press at 23000 lb/inch² and the precipitate is separated off. NH₄Cl (final concentration 0.1 mol/l) is added to the supernatant. The nucleic acids are removed by Polymin precipitation. Subsequently the centrifuged supernatant is fractionated on a heparin-Sepharose column. A gradient of 0-1 mol/l NaCl is used for the elution. SwaI is found in the fractions between 0.4 and 0.6 mol/l NaCl. The active fractions are equilibrated against buffer B (40 mmol/l Tris-HCl, pH 8.0, 0.1 mmol/l EDTA, 7 mmol/l 2-mercaptoethanol, 10% (w/v) glycerol) and fractionated on a DEAE fast-flow column. A gradient of 0-0.5 mol/l NaCl is used for the elution. The active fractions are dialyzed against buffer B.

They are subsequently applied to a cellulose phosphate column which was equilibrated with buffer B. A gradient of 0-1 mol/l NaCl in buffer B is used for the elution. SwaI is found in the fractions between 0.3 and 0.5 mol/l NaCl.

The active fractions are pooled and dialyzed against storage buffer (20 mmol/l Tris-HCl, pH 8.0, 10 mmol/l 2-mercaptoethanol, 100 mmol/l NaCl, 0.1 mmol/l EDTA and 50% (v/v) glycerol).

EXAMPLE 2

Determination of the Activity

Definition of the enzyme units: 1 U SwaI cleaves 1 μg adeno 2 DNA within 1 hour at 25° C. in 25 μl final volume.

17.9 μl water and 3.6 μl adeno 2 DNA (optical density: 5.6 OD/ml) as well as 1 μl SwaI solution (1 U/μl) are added to a mixture of 2.5 μl incubation buffer (500 mmol/l Tris-HCl, pH 7.5, 37° C., 100 mmol/l magnesium chloride, 1 mol/l NaCl and 10 mmol/l DTE). The solution is incubated for 1 hour at 25° C., cooled on ice and 5 μl of a terminating reagent consisting of 7 mmol/l urea, 20% (w/v) saccharose, 60 mmol/l EDTA and 0.01% (w/v) bromophenol blue is added. Subsequently a separation is carried out by electrophoresis in 1% agarose gels for 3-4 hours at 100 V. The bands obtained are identified by comparison with a DNA length standard.

We claim:

1. Type II restriction endonuclease having the recognition sequence

and the cleavage site indicated by the line.

2. Type II restriction endonuclease of claim 1, obtained from microorganisms of the genus *Staphylococcus*.

3. Restriction endonuclease of claim 1, obtained from *Staphylococcus warneri* DSM 5872.

4. Restriction endonuclease of claim 1, characterized by a temperature optimum at 25° C. and a pH optimum at 7.5.

5. Process for the isolation of a type II restriction endonuclease having the recognition sequence

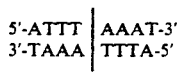

and the cleavage site indicated by the line comprising culturing microorganisms of the genus *Staphylococcus* and isolating the enzyme from the cells.

6. Process of claim 5, wherein *Staphylococcus warneri* DSM 5872 is cultured.

7. Process of claim 5, further comprising lysing said cells and isolating the cell supernatant.

8. Process of claim 7, further comprising subjecting said cell supernatant to affinity chromatography and to ion-exchange chromatography.

9. Process of claim 8, wherein said affinity chromatography is carried out using carrier-bound heparin.

10. Method for obtaining a DNA fragment with a sequence selected from the group consisting of:

5'... ATTT-3'
3'... TAAA-5' and

5' AAAT... 3'
3' TTTA... 5' comprising contacting a double stranded DNA molecule with the type II restriction endonuclease of claim 1 under conditions favoring cleavage of said double stranded DNA molecule and obtaining DNA fragments therefrom.

* * * * *